United States Patent
George et al.

(10) Patent No.: US 6,808,489 B2
(45) Date of Patent: Oct. 26, 2004

(54) PENILE PROSTHESIS WITH IMPROVED REAR TIP EXTENDER

(75) Inventors: Stephanie A. George, St. Paul, MN (US); Ginger Sackett Glaser, Little Canada, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/422,486

(22) Filed: Apr. 25, 2003

(65) Prior Publication Data

US 2003/0220539 A1 Nov. 27, 2003

Related U.S. Application Data

(60) Provisional application No. 60/383,464, filed on May 24, 2002.

(51) Int. Cl.[7] .................................................. A61F 5/00
(52) U.S. Cl. ........................................................ 600/40
(58) Field of Search ........................ 600/38–41, 29–31; 128/897, 899, DIG. 25; 623/11.11, 23.64, 23.67, 66.1

(56) References Cited

U.S. PATENT DOCUMENTS 4,602,621 A * 7/1986 Hakky .......................... 600/40
5,050,592 A * 9/1991 Olmedo ........................ 600/40

* cited by examiner

Primary Examiner—Samuel G. Gilbert

(57) ABSTRACT

The present disclosure is directed to an improved rear tip and rear tip extender where the rear tip securely attaches to a rear tip extender, even when slippery, and can avoid creating an irritating discontinuity in the profile. In a first aspect, the disclosure is directed to a penile implant having a cylinder with a rear tip. The rear tip includes a section having a generally smooth profile and a section having a connector end. A rear tip extender is adapted to fit over the section having the connector end. The rear tip extender includes a base, wherein the base fits over the rear tip at an interface. The rear tip is adapted to receive the rear tip extender with a ring in groove attachment. The base is aligned with the generally smooth profile of the rear tip without a protuberance at the interface. In a second aspect, the disclosure is directed to a penile implant including a cylinder having a rear tip. The cylinder includes a hydrophilic coating adapted to receive an antimicrobial solution. A rear tip extender is adapted to fit over the rear tip, and the rear tip and rear tip extender are connected together with a ring in groove attachment.

12 Claims, 3 Drawing Sheets

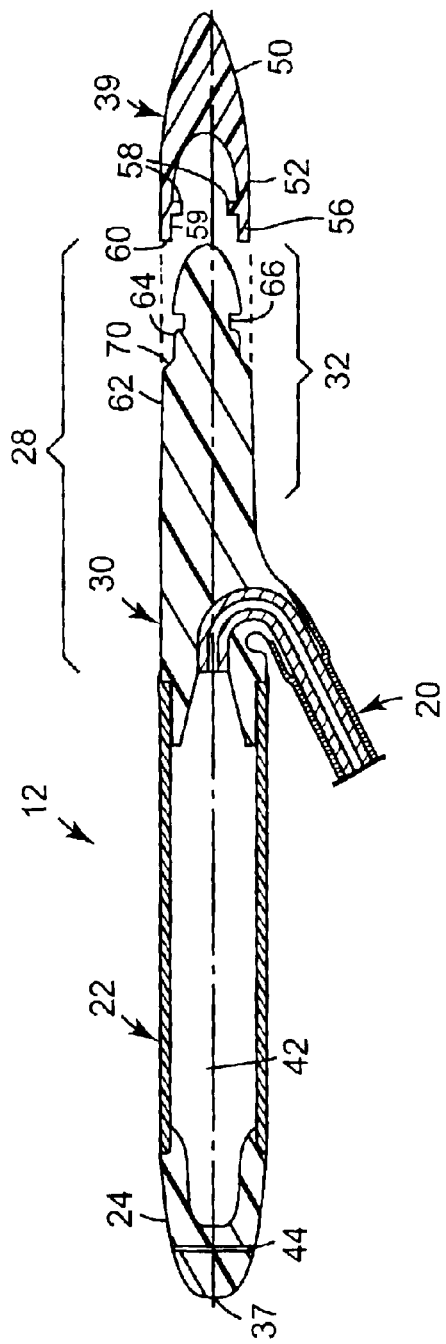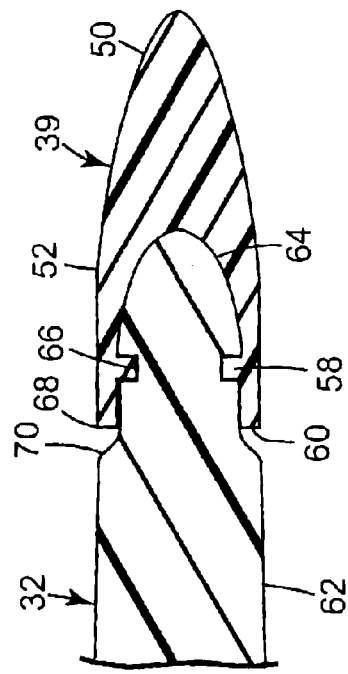

PENILE PROSTHESIS WITH IMPROVED REAR TIP EXTENDER

REFERENCE TO CO-PENDING APPLICATION

This patent application claims priority to co-pending United States provisional application for patent filed on May 24, 2002, having Ser. No. 60/383,464, and titled "Surgical Instruments and Methods."

BACKGROUND

The present disclosure relates to medical devices used in implant surgery. More specifically, the present disclosure relates to a penile prosthesis, or penile implant, adapted to receive rear tip extenders.

The study of impotence has recently become center stage in the field of medicine. In the early 1970's, the conventional view was that ninety percent of impotence cases were psychologically based, whereas only ten percent of the cases were caused by a physical condition. Today, doctors and scientists understand that the overwhelming majority of cases are caused by a physical condition. Accordingly, more and more resources are poured into the study of and treatment for impotence. In a recent study, fifty-two percent of men between the ages of forty and seventy self-reported that they suffer from some type of erectile dysfunction. Another study estimated that over thirty million American men and their partners suffer from erectile dysfunction.

Advertisements for pharmaceutical treatments for impotence have become ubiquitous, and include endorsements from celebrities that suffer from erectile dysfunction. More and more men and their partners now are seeking treatment for impotence. In the recent past, it was estimated that only one in twenty sufferers of erectile dysfunction sought treatment from their doctors. Pharmaceutical treatments are successful for only a subset of impotence sufferers. More invasive treatments are necessary for many men. These treatments include injection therapy, vacuum devices and penile prostheses.

For many impotence sufferers, the penile implant is the only solution to restore a happy and healthy sex life. The penile implant has been used for decades and provides a selected and reliable erection. The penile implant includes a pair of cylinders. In some instances, these cylinders are inflatable, and are connected to a fluid-filled reservoir with a pump and valve assembly. The two cylinders are normally implanted into the corpus cavernosae of the patient's penis and the reservoir is typically implanted into the patient's abdomen. The pump assembly is implanted in the scrotum. During use, the patient actuates the pump and fluid is transferred from the reservoir through the pump and into the cylinders. This results in the inflation of the cylinders and produces rigidity for a normal erection. Then, when the patient desires to deflate the cylinders, a valve assembly within the pump is actuated in a manner such that the fluid in the cylinders is released back into the reservoir. This deflation returns the penis to a flaccid state.

A type of inflatable penile implant includes two cylinders each having an inflation chamber side that is disposed within the penis (distal corpus cavernosae) and rear tip side that is disposed within the body (proximal corpus cavernosae.) The penile implant includes a remote pump assembly that is connected via tubing to the cylinders. Fluid is transferred from the pump assembly, through the tubing, and into the inflation chambers. The rear tip is not inflated.

The penile prosthesis is an invasive treatment and requires a delicate and painful surgery to implant. To reach the corpus cavernosae and implant the cylinders, the surgeon will first make an incision at the base of the penis, such as where it meets the scrotum. The patient is prepared for the cylinder after the surgeon has dilated each corpus cavernosum to create space for the cylinders. The distal end of the cylinder, i.e., the inflation chamber, is inserted into the corpus cavernosum. The proximal end of the cylinder, i.e., the rear tip, is inserted back into the body toward the pubic bone. To ensure a proper fit, the surgeon may choose to attach one or more rear tip extenders to the rear tip. One example of a rear tip extender is a silicone rubber cap that fits onto the rear tip or another rear tip extender that will provide the proper length of the cylinder.

A concern during implant surgery is infection around the prosthesis. One straightforward method of reducing the chances of infection is to impregnate antibiotics into the tissue-contacting surfaces of the prosthesis. One such antibiotic formulation is minocycline hydrochloride and rifampin. A second method is to coat the tissue-contacting surfaces of the prosthesis with a hydrophilic material. Prior to implantation, the surgeon will soak the prosthesis in an antimicrobial solution such as a bath including a bacteriostatic product like poly vinyl pyrollidone (PVP). The hydrophilic material will hold the solution on the surface of the prosthesis. This second method, however, suffers from some disadvantages. For example, the prosthesis becomes slippery when soaked in the antimicrobial solution. The prosthesis is more slippery than one with impregnated antibiotics from the first method, and is more slippery than one without a surface treatment.

A slippery prosthesis can cause problems when used with rear tip extenders. Prostheses applying the second method use slide-on friction-fit rear tip extenders. These extenders look like hollow versions of the tapered rear tip, or hollow cones. The hollow cones slide on the end of the rear tip and stay on because of the friction created with the rear tip against the inside of the cone. Surgeons have determined that in some cases, the rear tip extender will slide off the rear tip of a prosthesis prepared with the second method. The rear tip extender then can be lost in the body.

Another difficulty of these rear tip extenders is that the shape itself can cause trauma to the patient in what otherwise is a very sensitive area. Imagine stacking a hollow cone on another cone. The stack is efficient, but there is not a smooth profile at the wide end of the hollow cone, i.e., the wide end of the rear tip extender. The discontinuity or protuberance at the end of the rear tip extender can cause trauma to the patient. This trauma is compounded if more than one rear tip extender is applied.

Accordingly, there is a need in the art for a less invasive rear tip extender that does not include an irritating discontinuity when attached to a prosthesis, and one that can be reliably attached to a slippery prosthesis after it has been soaked in a antimicrobial solution.

SUMMARY

The present disclosure is directed to an improved rear tip and rear tip extender where the rear tip securely attaches to a rear tip extender, even when slippery, and can avoid creating an irritating discontinuity in the profile.

In a first aspect, the disclosure is directed to a penile implant having a cylinder with a rear tip. The rear tip includes a section having a generally smooth profile and a section having a connector end. A rear tip extender is adapted to fit over the section having the connector end. The rear tip extender includes a base, wherein the base fits over the rear tip at an interface. The rear tip is adapted to receive the rear tip extender with a ring in groove attachment. The base is aligned with the generally smooth profile of the rear tip without a protuberance at the interface.

In a second aspect, the disclosure is directed to a penile implant including a cylinder having a rear tip. The cylinder includes a hydrophilic coating adapted to receive an antimicrobial solution. A rear tip extender is adapted to fit over the rear tip, and the rear tip and rear tip extender are connected together with a ring in groove attachment.

BRIEF DESCRIPTION OF THE FIGURES

FIG. 3 is a side sectioned view of a portion of the penile implant of FIG. 2.

FIG. 4 is an enlarged side sectioned view of the portion of the penile implant of FIG. 3.

DESCRIPTION

This disclosure relates to penile prostheses or penile implants adapted to accept a rear tip extender. The disclosure, including the figures, describes the penile implants and rear tip extenders with reference to a several illustrative examples. Other examples are contemplated and are mentioned below or are otherwise imaginable to someone skilled in the art. The scope of the invention is not limited to the few examples, i.e., the described embodiments of the invention. Rather, the scope of the invention is defined by reference to the appended claims. Changes can be made to the examples, including alternative designs not disclosed, and still be within the scope of the claims.

Figure 1:
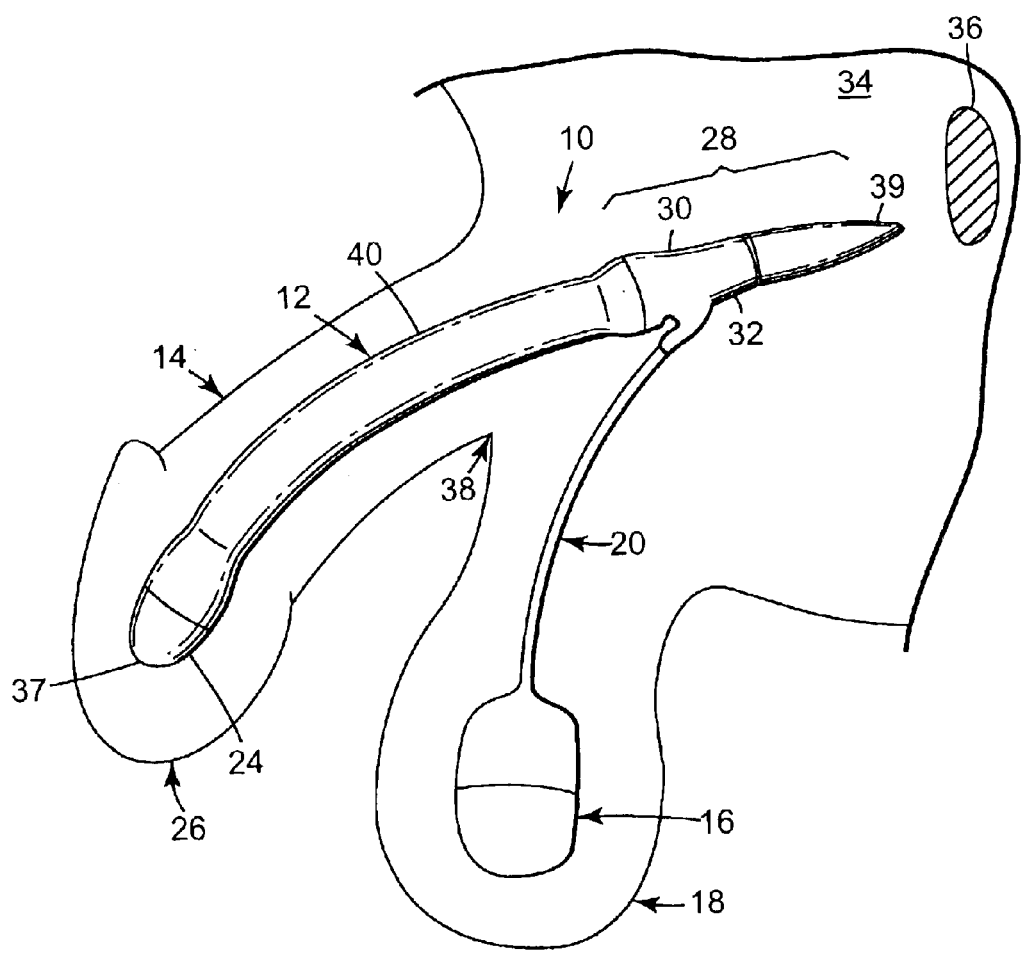
FIG. 1 is a schematic side view of a penile prosthesis implanted in a patient.

FIG. 1 is a schematic side view of a penile prosthesis 10 implanted in a patient. The prosthesis 10 includes a pair of cylinders, of which only one cylinder 12 is shown, implanted in a penis 14. The prosthesis can also include a pump 16, often implanted into the patient's scrotum 18. The tubing 20 attaches the pump 16 to the cylinder such that the pump 16 is in fluid communication with the cylinder 12. In still an alternative example, the pump 16 can be in fluid communication with a fluid reservoir (not shown) that is often implanted into the patient's abdomen. The prosthesis including a pair of cylinders, pump, and fluid reservoir is referred to as a three-piece device. In the present example, the prosthesis 10 includes cylinders 12 and a pump 16 and is known as a two-piece device. Still, in some examples, the pump and fluid reservoir are included within the cylinders. These are known as single piece devices. Some devices do not include a pump and a fluid reservoir. In these devices the cylinders do not inflate and are malleable. The disclosure predominantly describes a two-piece device, but one skilled in the art can easily recognize the applicability of this disclosure to other penile implants.

The cylinder 12 includes an inflation chamber 22 that is disposed within the penis 14. The distal end 24 of the cylinder 12 is disposed within the crown 26 portion of the penis 14. The cylinder also includes a proximal end 28 that often includes the tubing junction 30, i.e., the structural portion of the cylinder 12 connected to the tubing 20, and the rear tip 32 of the cylinder 12. The proximal end 28 is typically implanted into the patient's pubic region 34 with the rear tip 32 having a rear tip extender 39 proximate the pubic bone 36.

Figure 2:
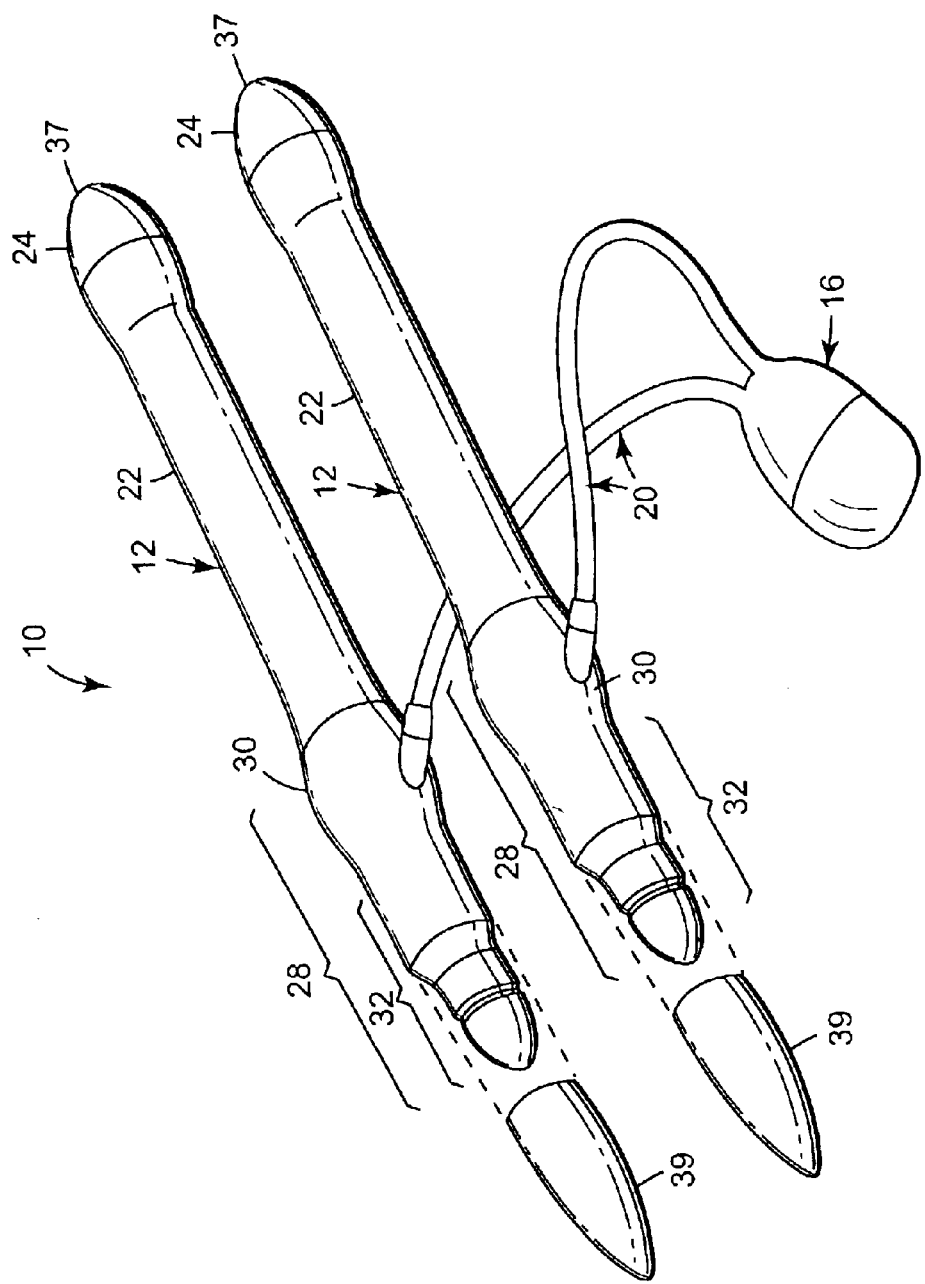
FIG. 2 is a perspective view of the penile prosthesis of FIG. 1.

The prosthesis 10 is shown by itself in FIG. 2. The prosthesis includes a pair of cylinders 12 connected by tubing 20 to a pump 16. Like parts of each cylinder are given the same reference number. Accordingly, the prosthesis 10 is a two-piece device. The prosthesis includes two cylinders 12, one for each side of the penis. Each cylinder includes a distal end 24 having a distal tip 37, an inflation chamber 22 and a proximal end 28 including a tubing junction 30, a rear tip 32 and a rear tip extender 39. The rear tip extender is an interchangeable piece that fits on the rear tip 32 and provides the appropriate length of the cylinder depending on the anatomy of the patient. The pump 16 serves to inflate both cylinders 12. In the case of a three-piece device, typically one fluid reservoir is connected in fluid communication with the pump.

In order to implant the cylinders 12, the surgeon first prepares the patient. The surgeon often makes an incision in the penoscrotal region 38, i.e., where the base of the penis 14 meets with the top of the scrotum 18. From the penoscrotal incision, the surgeon will dilate the patient's corpus cavernosum 40 (the distal corpus cavernosae) to prepare the patient to receive the cylinders 12. The corpus cavernosum is one of two parallel columns of erectile tissue forming the dorsal part of the body of the penis 14, i.e., two slender columns that extend substantially the length of the penis. The surgeon will also dilate two regions of the pubic area (the proximal corpus cavernosae) to prepare the patient to receive the proximal ends 28. The surgeon will measure the length of the corpus cavernosum from the incision and the dilated region of the pubic area to determine an appropriate length of the cylinders 12 and rear tip extenders 39 to implant.

After the patient is prepared, the prosthesis 10 is implanted into the patient. The distal tip 37 of each cylinder often is attached to a suture. The other end of the suture is often then attached to a Keith needle. The Keith needle is inserted into the incision and into the dilated corpus cavernosum. The Keith needle is then advanced through the crown of the penis. The surgeon tugs on the suture to pull the cylinder into the corpus cavernosum. This is done for each cylinder. Once the inflation chamber 22 is in place, the surgeon removes the suture from the distal end 37. The surgeon then inserts the proximal end 28. The surgeon inserts the rear tips 32, with rear tip extenders if needed, into the incision and forces the proximal ends 28 toward the pubic bone 36 until the cylinders are in place.

FIG. 3 shows a side sectioned view of one of the cylinders 12 and includes distal end 24 and proximal end 28. The cylinder 12 includes an axis 42. The distal end 24 forms part of the inflation chamber 22. The distal end 24 is generally solid but can include a hole 44 that is adapted to receive the suture described above. In the example, the distal end 24 is constructed from a silicone rubber or silicone elastomer. The inflation chamber 22 in the example includes a multilayer tube. The example includes three layers and an outer coating. The innermost layer is an extruded silicone elastomer, the middle layer is a distensible fabric such as a polyester and spandex blend, and the outer layer is also an extruded silicone. The outer coating in the example is parylene. Parylene coating is a medical grade polymer intended to reduce friction-based wear occurrences. Parylene can be applied to other layers as is known in the art.

In addition, the prothesis can be coated with a hydrophilic material as is known in the art. One such material is described in U.S. Pat. No. 5,295,978 titled "Biocompatible Hydrophilic Complexes and Process for Preparation and Use" and assigned to the Union Carbide Chemicals and Plastics Technology Corporation of Danbury, Conn. In short, the hydrophilic complexes are comprised of a carboxylic acid polymer with either a poly(lower-alkylene oxide) or a poly(N-vinyl lactam). A complex of an antimicrobial agent such as iodine can be formed with the hydrophilic complex to provide antimicrobial activity. The hydrophilic complex is particularly suitable for forming biomedical coatings on the prosthesis. The hydrophilic complex also has the property of rendering the surface of the prosthesis lubricious (slippery) when exposed to aqueous solutions, such as the antimicrobial solution and body fluids.

The proximal end 28 includes the rear tip 32 and the tubing junction 30. In the example, the rear tip 32 is solid and formed from a silicone rubber or silicone elastomer. The rear tip can also include barium sulfate, so that it can be easily visible in an X-Ray of the region. The barium sulfate can also be added to other parts of the prosthesis including the rear tip extender 39 for the same purpose. Alternatively, other radio-opaque markers, such as aluminum oxide or iridium, can be used. The rear tip 32 is adapted to receive the rear tip extender 39. The rear tip 32 and rear tip extender 39 are described in more detail with reference to FIGS. 3 and 4.

FIG. 4 is an enlarged view of FIG. 3 showing a portion of the proximal end 28 and the rear tip extender 39. The rear tip extender 39 includes a generally solid tip portion 50 and a hollow skirt 52. The skirt 52 fits over the rear tip 32.

The tip portion 50 is abutted against the rear tip 32. In these examples, the tip portion 50 provides the extra length. A typical rear tip extender 39 can add between 0.5 centimeters to several centimeters in length to the cylinder. The skirt 52 includes a wall 56 having a thickness. The rear tip extender 39 of the example includes a ring 58 that protrudes from the inner surface 59 of the skirt wall 56 proximate the base 60 of the skirt.

The rear tip 32 in the example includes a first section 62 having a generally smooth profile and a second section having a connector end 64. The connector end 64 is adapted to fit within the rear tip extender 39, and the smooth profile first section 62 is adapted to fit against the patient. The diameter of the connector end 64 is smaller than the diameter of the proximate first section 62. The difference in diameter between the proximate first section and the connector end is approximately the thickness of the wall 56 at the base 60 of the skirt of the rear tip extender. Preferably, the difference is about the same or greater than the thickness of the wall 56 of the rear tip extender 39. The connector end 64 in the example includes a groove 66. The groove 66 mates with the ring 58 to securely attach the rear tip extender 39 onto the rear tip 32.

The rear tip is attached to the rear tip extender with a "ring in groove" attachment. In the example shown, the rear tip 32 includes a full groove 66 and is adapted to fit a full ring 58 on the rear tip extender 39. Variations of this are contemplated. For example the rear tip could include the ring and the rear tip extender could include the groove. The ring or groove on either example need not be full, or all the way around the perimeter, but could only be partially around the perimeter, or selectively around the perimeter. Also, the ring and groove could be replaced with at least one indent mating with at least one detent. For the purposes of this disclosure, attachments using indents and detents are a form of ring in groove attachment.

The first section 62 having the generally smooth profile meets the base 60 of the rear tip extender at an interface 68. The rear tip extender is aligned with the generally smooth profile of the first section 62. In one example, the base 60 is immediately proximate, or in contact with the first section 62. In the example shown, however, the base 60 is spaced-apart from the first section 62. The rear tip 32 includes an angled transition section 70 used to space apart the base 60 from the first section 62. A small indent exists in the profile at the transition section 70.

The transition section 70 is provided in the example to reduce wear between the skirt 52 and the first section 62 of the rear tip. When disposed inside the body, the proximal end 28 is not axial as shown in FIG. 3, but more curved or bent as indicated in FIG. 1. Accordingly, one side of the skirt 52 is closer to the first section 62 than the opposite side of the skirt 52. The transition section 70 is provided to account for this configuration. In examples of the related art, the transition section was angled upward at a maximum of 45 degrees from the connector end to the first section. In cases where the rear tip extender was of a slide on type, the "transition section" starts at the interface and ends at the point where the diameter of the rear tip is the same as the diameter of the base of the skirt. The angle in the slide-on example is substantially less than 45 degrees. The angle is measured from the connector end to the first section relative to the axis.

Angles of 45 degrees or less cause substantial discontinuities in the profile of the proximal end 28 when a rear tip extender 39 is attached. These discontinuities are considered in this disclosure to be protuberances. The protuberance can cause irritation to the surrounding tissues of the body during surgery or after implant.

The wear created between the rear tip 32 and the rear tip extender 39 is not as large an issue as previously believed. The transition section 70 in the examples is angled at greater than about 45 degrees, and preferably about 60 degrees to reduce the space of the indent in the transition section 70. The transition section 70 having an angle of greater than 45 degrees creates a substantially smooth profile when the diameters of the first section 62 and the base 60 of the skirt are substantially the same. In this configuration, the transition section 70 does not include a length to create an indent that would substantially irritate the surrounding tissue.

In this example, the transition section 70 is not substantial in length and thus continues the generally smooth profile of the first section 62. In addition, the interface provides only an indent in the profile. For the purposes of this disclosure an indent at the transition section 70 still continues the generally smooth profile of the rear tip. The rear tip does not provide a protuberance to the generally smooth profile. In other words, the rear tip extender is not wider in diameter than the first section by at least the thickness of the wall at the interface. In the example shown, the wide end of the rear tip extender is not larger in diameter than the smallest diameter of the first section.

The present invention has now been described with reference to several embodiments. The foregoing detailed description and examples have been given for clarity of understanding only. Those skilled in the art will recognize that many changes can be made in the described embodiments without departing from the scope and spirit of the invention. Thus, the scope of the present invention should not be limited to the exact details and structures described herein, but rather by the appended claims and equivalents.

What is claimed is:

1. A penile implant, comprising:
   a cylinder having a rear tip, wherein the rear tip includes a first section having a generally smooth profile and a section having a connector end; and a rear tip extender adapted to fit over the section having the connector end, the rear tip extender having a base, wherein the base fits over the rear tip at an interface;

wherein the rear tip is adapted to receive the rear tip extender with a ring in groove attachment and wherein the base is aligned with the generally smooth profile of the rear tip without a protuberance at the interface.

2. The penile implant of claim 1 wherein the rear tip further includes a transition section disposed between the first section and the connector end.

3. The penile implant of claim 2 wherein the transition section extends from the connector end to the first section at an angle of greater than 45 degrees relative to an axis of the cylinder.

4. The penile implant of claim 3 wherein the angle is 60 degrees.

5. The penile implant of claim 1 wherein the cylinder includes an inflation chamber.

6. The penile implant of claim 5 wherein the penile implant includes a pump in fluid communication with the inflation chamber.

7. The penile implant of claim 1 wherein the cylinder includes a hydrophilic coating adapted to receive an antimicrobial solution.

8. The penile implant of claim 1 wherein the ring and groove attachment includes the rear tip extender having a ring and the connector end having a groove adapted to receive the ring.

9. The penile implant of claim 1 wherein the base includes a base diameter and the first section includes a first section diameter, and wherein the base diameter is equal to or less than the first section diameter.

10. A penile implant, comprising:

a cylinder having a rear tip, wherein the cylinder includes a hydrophilic coating adapted to receive an antimicrobial solution; and a rear tip extender adapted to fit over the rear tip, wherein the rear tip and rear tip extender are connected together with a ring in groove attachment.

11. The penile implant of claim 10 wherein the hydrophilic coating includes a carboxylic acid polymer with either a poly(lower-alkylene oxide) or a poly(N-vinyl lactam).

12. The penile implant of claim 10 wherein the rear tip includes a first section and a connector end, wherein the rear tip extender is adapted to receive the connector end.

* * * * *